United States Patent [19]
McGee et al.

[11] Patent Number: 5,984,907
[45] Date of Patent: Nov. 16, 1999

[54] TRANSITION SLEEVE ASSEMBLY FOR CATHETERS

[75] Inventors: David McGee, Sunnyvale; Jamil Ahmad, San Jose; Thomas M. Bourne, Mountain View; Michael Idaomi; Simplicio Velilla, both of Sunnyvale; David K. Swanson, Mountain View, all of Calif.

[73] Assignee: EP Technologies, Inc., Sunnyvale, Calif.

[21] Appl. No.: 08/462,347

[22] Filed: Jun. 5, 1995

[51] Int. Cl.⁶ ................................................. A61M 25/00

[52] U.S. Cl. ........................ 604/282; 604/264; 604/280; 604/95

[58] Field of Search .............................. 604/95, 280, 281, 604/282; 6007/115, 116, 141

[56] References Cited

U.S. PATENT DOCUMENTS 5,308,342  5/1994  Sepetka et al. ........................ 604/282
5,328,467  7/1994  Edwards et al. .......................... 604/95

Primary Examiner—Wynn Wood Coggins
Assistant Examiner—N. Kent Gring
Attorney, Agent, or Firm—Lyon & Lyon LLP

[57] ABSTRACT

A sleeve assembly for use in the transition region of a catheter between a relatively stiff catheter body and a less stiff distal catheter region mediates the difference in stiffness between these two catheter regions.

26 Claims, 4 Drawing Sheets

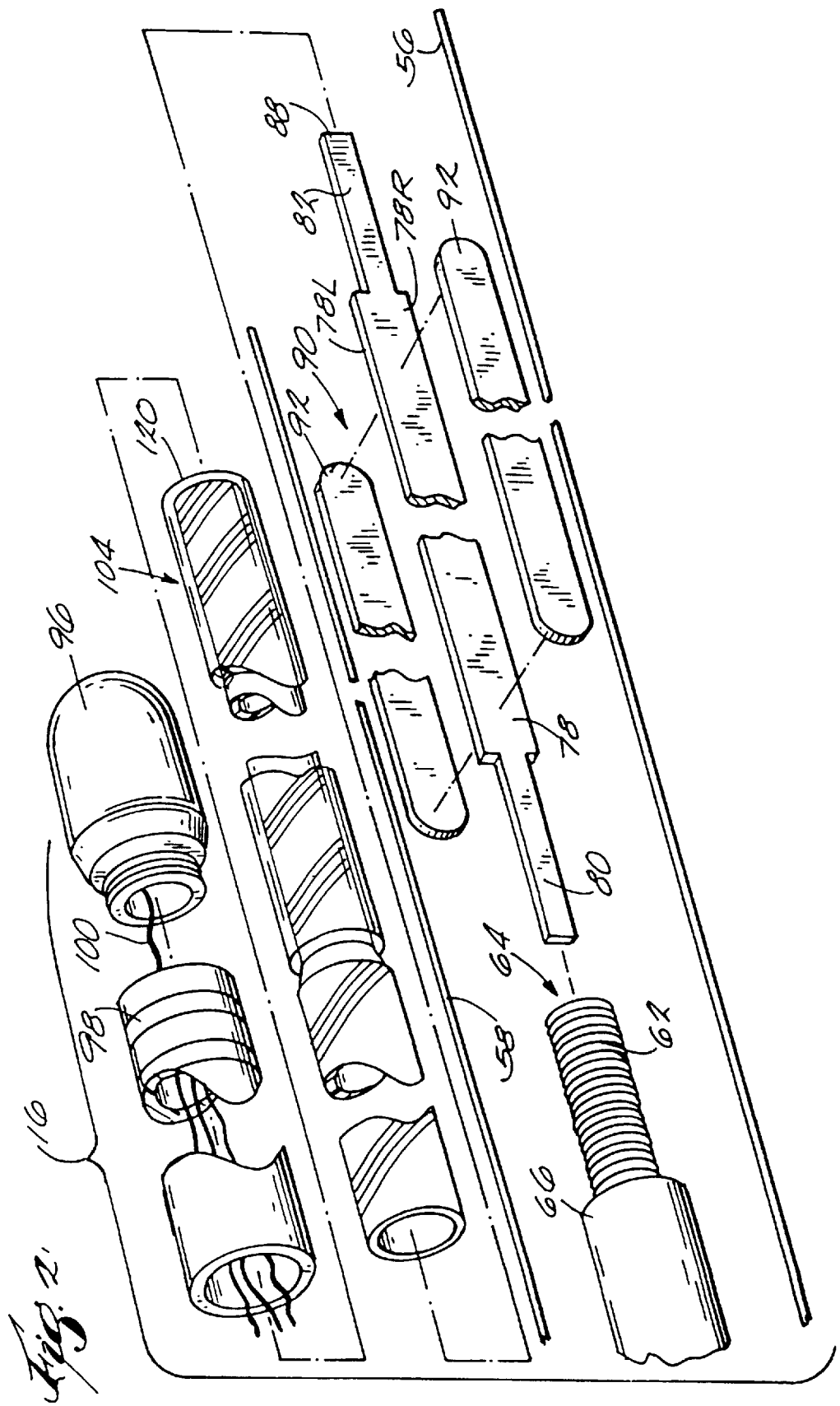

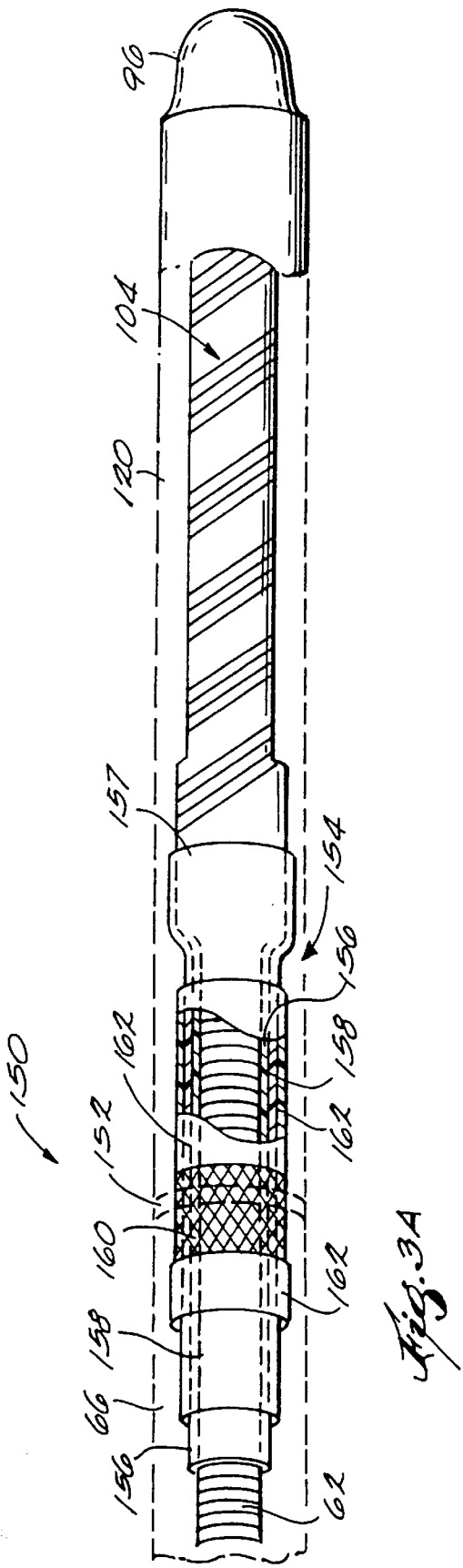
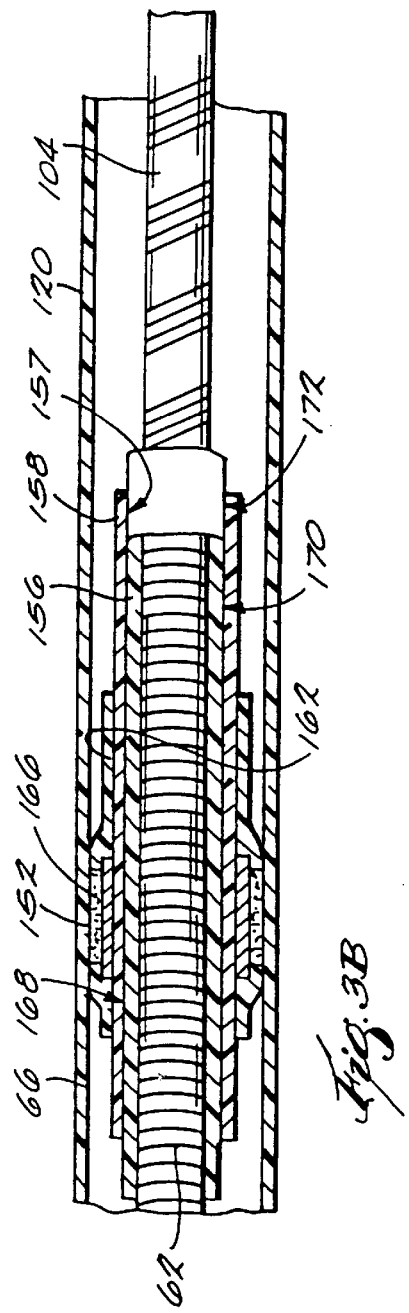

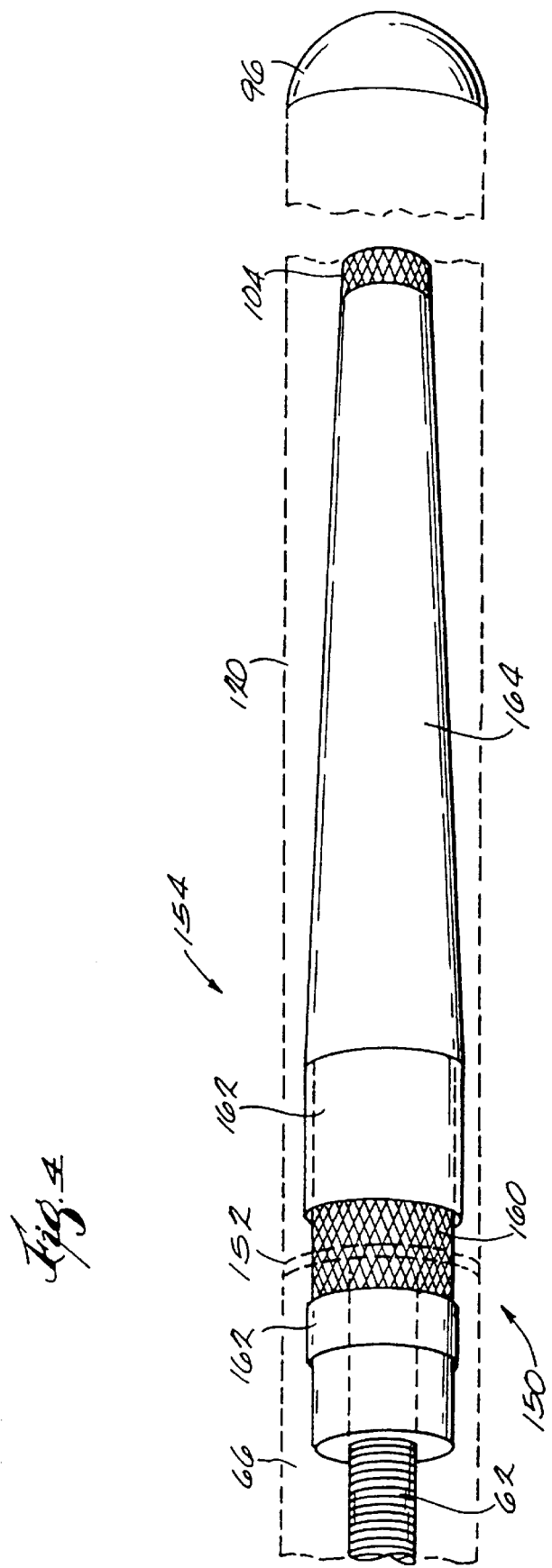

TRANSITION SLEEVE ASSEMBLY FOR CATHETERS

FIELD OF THE INVENTION

The invention generally relates to catheters. In a more specific sense, the invention relates to catheters that can be steered and manipulated within interior regions of the body from a location outside the body.

BACKGROUND OF THE INVENTION

Physicians make widespread use of catheters today in medical procedures to gain access into interior regions of the body. It is important that the physician can control carefully and precisely the movement of the catheter within the body.

The need for careful and precise control over the catheter is especially critical during procedures that ablate tissue within the heart. These procedures are becoming more widespread for treating cardiac rhythm disturbances.

During these procedures, a physician steers a catheter body through a main vein or artery (which is typically the femoral arterial) into the interior region of the heart that is to be treated. The physician then further manipulates a steering mechanism to place the electrode carried on the distal end of the catheter body into direct contact with the tissue that is to be ablated. The physician transmits radio frequency energy from the electrode tip to ablate the tissue and form a lesion.

Catheters for cardiac ablation and similar procedures involving inter-vascular access require a catheter body with requisite flexibility yet stiffness to maneuver through sometimes tortuous vascular paths. At the same time, these catheters require a distal end with the requisite flexibility without stiffness to be accurately steered into contact with a local tissue region. These two requirements, one for stiffness over flexibility to meet a first important set of criteria, and another for flexibility over stiffness to meet a second, equally important set of criteria, create a transition region in the catheter where the relatively stiff catheter body joins the less stiff and more flexible catheter distal end.

SUMMARY OF THE INVENTION

The invention provides a sleeve assembly to graduate the transition in stiffness between a relatively stiff catheter body and a less stiff distal catheter region.

In a preferred embodiment, the transition sleeve assembly includes a layered body spanning the connection between the catheter body and the distal region. A first layer is attached to the catheter body. A second layer overlies the first layer and also overlaps a portion of the distal region.

In a preferred embodiment, a junction joins a first sleeve that surrounds the catheter body to a second sleeve that surrounds the distal region. In this embodiment, the transition sleeve assembly underlies the junction. In this embodiment, the transition sleeve assembly also includes a mesh of increased tensile strength that underlies the junction to strengthen it.

The apparatus that embody the features of the invention are well suited for use in the field of cardiac ablation. They also are applicable for use in other applications requiring inter-vascular access. For example, the various aspects of the invention have application in procedures for accessing tissue in the prostrate, brain, gall bladder, uterus, and other regions of the body.

Other features and advantages of the inventions are set forth in the following Description and Drawings, as well as in the appended claims.

BRIEF DESCRIPTION OF THE DRAWINGS

FIG. 2 is an exploded view of the electrode tip assembly of the catheter;

FIG. 3A is an enlarged perspective view of the transition sleeve assembly located between the catheter body assembly and electrode tip assembly of the catheter, which embodies the features of the invention;

FIG. 3B is a side section view of the transition sleeve assembly shown in FIG. 3A, taken generally along line 3B—3B in FIG. 1; and FIG. 4 an enlarged perspective view of an alternative embodiment for the transition sleeve, which embodies the features of the invention.

Figure 1:
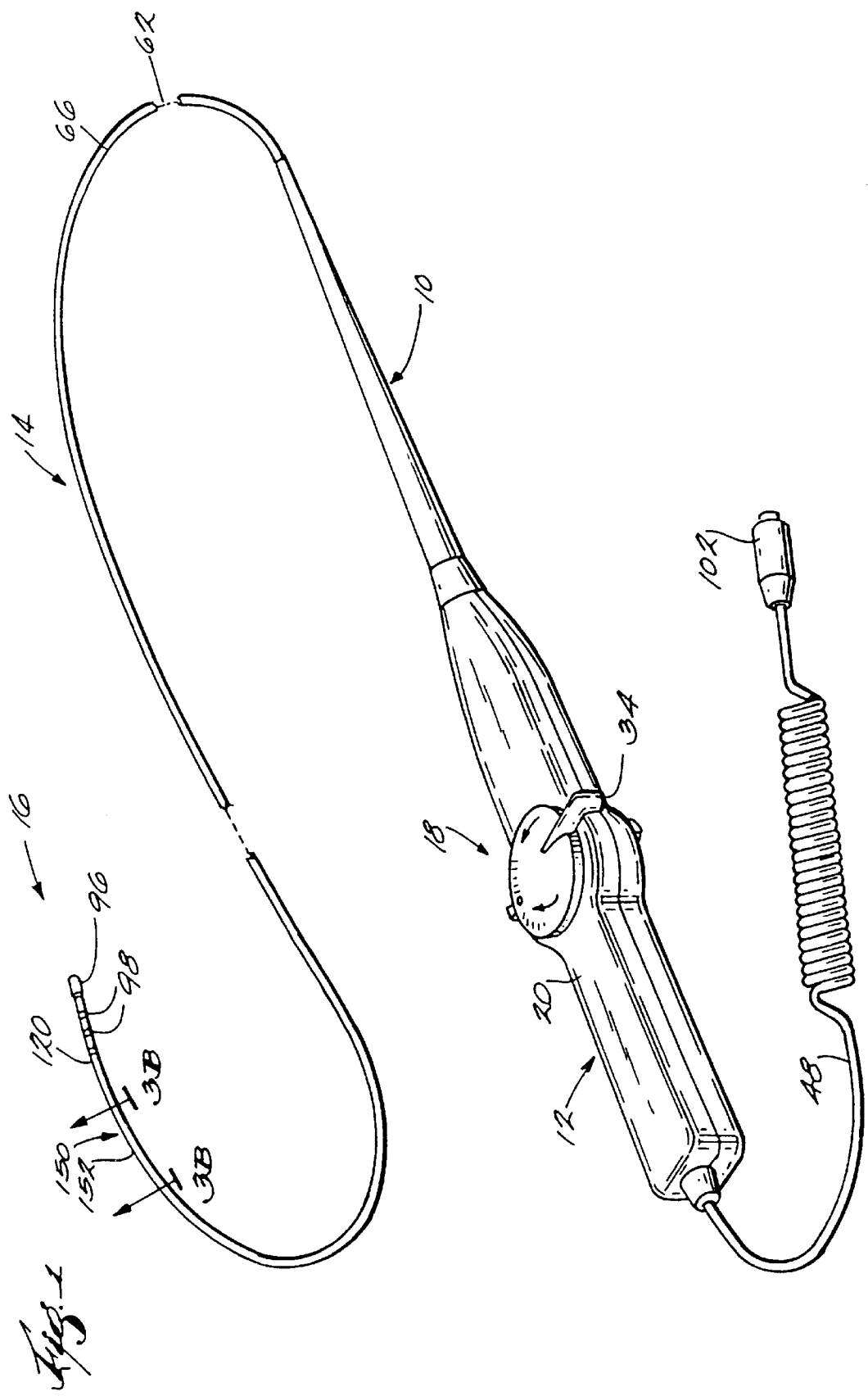
FIG. 1 is a perspective view of a catheter that embodies the features of the invention.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

FIG. 1 shows the assembly of a steerable catheter 10 that embodies the features of the invention. As there shown, the catheter 10 includes three main parts or assemblies: the handle assembly 12, the catheter body assembly 14, and the electrode tip assembly 16.

The catheter 10 can be used in many different environments. This specification will describe the catheter 10 as used for diagnostic or therapeutic purposes in the interior regions of the heart.

When used for this purpose, a physician grips the handle assembly 12 to maneuver the catheter body assembly 14 through a main vein or artery (which is typically the femoral arterial) into the interior region of the heart that is to be treated. The physician then further operates a steering mechanism 18 on the handle assembly 12 to selectively flex the electrode tip assembly 16 until desired contact is made with the tissue that is to be diagnosed or ablated.

As FIG. 1 shows, the handle assembly 12 includes a housing 20 that encloses a steering mechanism 18. The steering mechanism 18 includes a rotating cam wheel (not shown) within the housing 20 coupled to an external steering lever 34. The proximal ends of right and left catheter steering wires 56 and 58 (which are shown in FIG. 2) are fastened to the cam wheel. The steering wires 56 and 58 extend through the catheter body assembly 14. The distal ends of the steering wires 56 and 58 are attached to the electrode tip assembly 16. Rotating the cam wheel to the left and right bends the electrode tip assembly 16, respectively, left and right.

Further details of the steering mechanism 18 are not essential to the invention, but can be found in U.S. Pat. Nos. 5,395,327 and 5,358,478, which are incorporated herein by reference.

As FIG. 2 shows, the catheter body assembly 14 includes a flexible shaft 62 attached to the handle assembly 12. The flexible shaft 62 encloses an interior bore 64. The steering wires 56 and 58 pass through the interior bore 64.

The shaft 62 is required to be flexible so that it can be resiliently bent without breaking or kinking. Still, the shaft 62 must possess a degree of stiffness for strength and to permit maneuvering and twisting during vascular access. In the embodiment shown in FIGS. 1 and 2, the shaft 62 comprises a length of stainless steel coiled into a flexible spring enclosing the interior bore 64. A braided sheath 66 of plastic material encloses the shaft 62.

Alternatively, for greater torque transmission, the shaft 62 can comprises a slotted, stainless steel tube, as disclosed, for example, in U.S. Pat. No. 5,315,996. The shaft 62 can also comprise a length of composite, high torque plastic tubing, such as made from PEBAX™ material.

The catheter body assembly 14 can be made in various lengths. In the illustrated, the catheter body assembly 14 is about 100 cm in length.

As FIG. 2 shows, the electrode tip assembly 16 includes a bendable main support wire 78 having left and right faces 78L and 78R. In the illustrated embodiment, the main support wire 78 is made of stainless steel flat wire stock in an elongated shape about 0.035 inch wide and about 0.005 inch thick. The main support wire 78 is about 3 inches in total length. Further details of the construction of the main support wire 78 are not essential to the invention, but can be found in U.S. Pat. No. 5,363,861, which is incorporated herein by reference.

The opposite ends of the main support wire 78 are cut away to form stepped shoulders 80 and 82. One stepped shoulder 80 fits within the distal end of the flexible catheter body shaft 62 to append the electrode tip assembly 16 to the guide tube assembly 14. The distal end of the left steering wire 58 is soldered to the left face 78L of the main support wire 78. The distal end of the right steering wire 56 is soldered to the right face 78R of the main support wire 78.

In the illustrated embodiment (see FIG. 2), the stiffness of the main support wire 78 is not uniform, but varies along its length. A stiffening spring assembly 90 stiffens the center support near the distal end of the guide tube shaft 62. The stiffening spring assembly 90 includes two leaf springs 92 that sandwich the main support wire 78 between them. Further details of this assembly are found in the above cited U.S. Pat. No. 5,363,861.

In the illustrated embodiment, the distal end of the electrode tip assembly 16 carries an ablation tip electrode 96 and three ring electrodes 98. Interior conducting wires 100 are connected to the tip electrode 96 and the three ring electrodes 98. The conducting wires 100 extend along the main support wire 78, through the interior bore of the catheter body shaft 62, and into the handle housing 20 to join the coaxial cable 48 that extends from the rear of the housing 20.

The coaxial cable 48 ends with plugs 102. The plugs 102 connect with appropriate conventional catheter control equipment (not shown). The conducting wires 100 transfer electrical current from the ring electrodes 98 indicative of electrical activity within the heart. The conducting wires 100 also transfer radio frequency energy to the tip electrode 96 to carry out ablation procedures within the heart.

A reinforcing sleeve assembly 104 attaches the electrode tip assembly 16 to the catheter body assembly 14. In the illustrated embodiment, the reinforcing sleeve assembly 104 includes an reinforcing fabric 116 Kevlar 49 Yarn (DuPont) encased within heat shrink medical grade TFE Teflon™ plastic tubing, which is shrunk in place about the main support wire 78 and distal end of the catheter body assembly 14. Further details of the reinforcing sleeve assembly are not essential to the invention, but are found in U.S. Pat. No. 5,257,451, which is incorporated herein by reference.

The reinforcing sleeve assembly 104 is flexible enough to accommodate the bending movement desired for the electrode tip assembly 16. The reinforcing sleeve assembly 104 provides added strength and resistance against wear and tear during repeated bending operations. The reinforcing sleeve assembly 104 also holds the steering wires 56 and 58 and conducting wires 100 in close intimate contact against the main support wire 78. The intimate contact prevents kinking and chafing of the steering wires 56 and 58 and conducting wires 100 during bending operations.

A distal tube 120 of flexible urethane material or the like surrounds the electrode tip assembly 16. The tip electrode 96 and ring electrodes 98 are attached to the conducting wires 100 and joined to the distal tube 120 by conventional methods to complete the electrode tip assembly 16.

The proximal end of the distal tube 120 and the distal end of the braided tube 66 abut about a region 150 (see FIGS. 3A and 3B) of the catheter body shaft 62 about 2 inches before the reinforcing sleeve assembly 104. A butt bond 152 joins the tube ends together in this region 150. The butt bond 152 can be formed in various ways.

For example, the butt bond 152 can be formed by use of adhesives. The butt bond 152 can also be formed is be formed by melting the tube ends together by heat, sonic, or radio frequency energy.

The physical characteristics of the catheter body assembly 14 and associated braided tube 66 lend stiffness and strength to transmit linear and twisting motions along the guide tube assembly 14 to the electrode tip assembly 16. On the other hand, the physical characteristics of the electrode tip assembly 16 and associated tube 120 accommodate the side to side flexing of the electrode tip assembly 16 relative to the catheter body assembly 14. A step discontinuity in stiffness occurs from the braided tube 66-side of the butt bond 152 to the distal tube 120-side of the butt bond 152. The butt bond 152 itself also creates additional stiffness in this region 150. This step discontinuity in stiffness can lead to disproportionate flexure of the electrode tip assembly 16 when the distal tip assembly 16 encounters close vascular spaces or pronounced curvatures, such as in the region of the aortic arch. The step discontinuity in stiffness causes a step discontinuity in flexure. Instead of flexing in proportion to the catheter body assembly 14 to follow the shape of the surrounding vascular space, the electrode tip assembly 16 is observed to sometimes bend disproportionately and jam against the vascular walls.

For this reason, a transition sleeve assembly 154 (see FIGS. 3A and 3B) underlies the tubes 66 and 120 in the butt bond region 150. The transition sleeve assembly 154 extends from the butt bond region 150 to a portion of the main support wire 78, which in the illustrated embodiment is itself surrounded by the reinforcing sleeve assembly 104. The transition sleeve assembly 154 stiffens the distal tube 120 extending from the butt bond region 150, created a graduated transition in stiffness between the two assemblies 14 and 16. The transition sleeve assembly 154 causes the distal tube 120 to be stiffer than it would otherwise be in a region extending distally from the butt bond 152, but still less stiff than the braided tube 66.

In the illustrated embodiment, see FIG. 3, the transition sleeve assembly 154 comprises layered lengths of polymeric tubing that accommodate flexure without kinking or failing, but which add to the stiffness of the distal tube 120 they underlie. Various types of polymeric tubing can be used, according to the transitional stiffness desired.

In the preferred embodiment, the assembly 154 includes a first length 156 of polyester or Teflon™ plastic heat-shrink tubing that encircles a the distal region of the catheter body assembly 14 about the shaft 62. The first length 156 underlies both the braided tube 66 and the distal tube 120 proximally and distally of the butt bond region 152.

The assembly 154 also includes a second length 158 of polyester or Teflon™ plastic heat-shrink tubing. The second length 158 overlies the first tubing length 156 along the same distal region of the catheter body assembly 14, creating in this region a multiple layer structure. The second length 158 also extends distally farther than first length 154 to overlap a portion of the reinforcing sleeve assembly 104 at the proximal end of the electrode tip assembly 16. The overlap is designated by numeral 157 in FIGS. 3A and 3B.

The first and second lengths 156 and 158 extend proximally to just beyond the butt bond region 150. The proximal extremity of the first length 156 extends somewhat farther than the proximal extremity of the second length 158.

The added stiffness given by the layered assembly 154 provides a graduated transition in stiffness to what would otherwise be a discontinuity in stiffness between the relatively stiff braided tube 66 and the relatively flexible distal tube 120. The layered assembly 154 imparts to the overall electrode tip assembly 16 resistance to extreme flexure and "jamming" in close vascular spaces or where pronounced curvatures are encountered.

In the illustrated and preferred embodiment (see FIGS. 3A and 3B), a sleeve 160 made of a flexible material that has a tensile strength greater than the distal tube 120 or braided tube 66 preferably directly underlies the butt bond 152. A non-rigid metal material like 304 Stainless Steel Mesh can be used. Alternatively, a woven non-rigid fabric material like Kevlar 49 Yarn can be used. Alteratively, a non-rigid thermal plastic material can be used. The material selected depends upon the tensile strength and degree of flexibility desired. Further details of strengthening an adhesive butt bond by proving an underlying non-rigid metal or woven fabric or thermal plastic material are disclosed in copending U.S. patent application Ser. No. 08/402,732, filed Mar. 13, 1995 and entitled "Flexible Bond for Sleeves Enclosing a Bendable Electrode Tip Assembly." Further details about strengthening a thermal butt bond by melting the ends of the tubes 66 and 120 about an underlying temperature resistant sleeve, preferably having imbedded spirally wound metallic wire, are disclosed in copending U.S. patent application Ser. No. 08/271,186, filed Jul. 7, 1994 and entitled "Catheter Component Bond and Method."

Oppositely spaced collars or dams 162 secure the sleeve 160 to the transition sleeve assembly 154. Adhesive can be used to hold the collars 162 in place. However, in the illustrated and preferred embodiment, the collars 162 are made of a heat-shrink plastic material, like polyester.

The dams 162 provide a tri-layer stiffness region 168 (see FIG. 3B) underlying the butt bond 152 and distal tube 120. Moving distally of the butt bond 152, the tri-layer stiffness region 168 gives way to a double layer stiffness region 170 at the distal end of the catheter tube assembly 14, underlying the distal tube 120. Moving still more distally, the double layer stiffness region 170 gives way to a single layer stiffness region 172 at the proximal end of the electrode tip assembly 16, underlying the distal tube 120. These successive, varying stiffness regions 168, 170, and 172 provide a graduated transition in stiffness, creating a gradual diminishing bending stiffness, along the distal tube 120 extending distally from the butt bond 152 to a region spaced from the butt bond 152.

The dams 162 hold adhesive material 166 (see FIG. 3B) to strengthen the butt bond 152.

Instead of comprising layered heat-shrink tubing, the transition sleeve assembly 154 could be a composite of two or more dissimilar materials, or a randomly arranged matrix of dissimilar materials. For example, the assembly 154 could comprise a fiber-polymer composite of Kevlar™ and a plastic polymer, like the reinforcing sleeve assembly 104. Alternatively, the assembly 154 could comprise a metal-plastic polymer composition.

For example, these implementations could comprise Kevlar™ or wire windings sandwiched in one or more layers of polymer materials. The windings could uniform or variable pitch, and cross-wound or counter-wound or step-wound or single-directional, according to the stiffness properties desired. Composite assemblies could be made to have the strength to eliminate the need for the mesh sleeve 160 beneath the butt bond 152.

In another alternative embodiment (see FIG. 4), the transition sleeve assembly 154 can comprise a preshaped sleeve 164 that achieves a desired stiffness profile along its length. For example (as FIG. 4 shows), the sleeve 164 is tapered from its proximal end to its distal end to provide a gradual diminishing bending stiffness.

Various features of the invention are set forth in the following claims.

We claim:

1. A catheter, comprising:

a first flexible body having a first stiffness, the first flexible body having a distal region, a second flexible body having a proximal region attached to the distal region of the first flexible body, the second flexible body having a second stiffness different than the first stiffness, thereby creating a step discontinuity in stiffness between the first and second bodies, and a transition assembly having a first portion underlying the distal region of the first flexible body and a second portion underlying the proximal region of the second flexible body to thereby create a graduated transition in stiffness between the first and second flexible bodies.

2. A catheter according to claim 1 wherein the second stiffness is less than the first stiffness.

3. A catheter according to claim 1 wherein the second flexible body carries at least one electrode.

4. A catheter according to claim 1 wherein the second flexible body carries at least one radio frequency transmitting ablation electrode.

5. A catheter according to claim 1 and further including an element to flex the second flexible element relative to the first flexible element.

6. A catheter comprising a first flexible body having a distal region, a first flexible sleeve enclosing the first flexible body, the first sleeve having a first stiffness, a second flexible body having a proximal region attached to the distal region of the first flexible body, a second flexible sleeve enclosing the second flexible body, the second flexible sleeve being joined to the first flexible sleeve adjacent the distal region of the first flexible body, thereby forming a junction, the second flexible sleeve having a second stiffness different than the first stiffness creating a step discontinuity in stiffness between the first and second bodies, and a transition assembly in the distal region of the first flexible body and the proximal region of the second flexible body and underlying the junction between the first and second flexible sleeves to create a graduated transition in stiffness between the first and second flexible sleeves.

7. A catheter according to claim 6
wherein the second flexible body carries at least one electrode.

8. A catheter according to claim 6
wherein the second flexible body carries at least one radio frequency transitting ablation electrode.

9. A catheter according to claim 6
and further including an element to flex the second flexible element relative to the first flexible element.

10. A catheter comprising
a first flexible body having a distal region,
a first flexible sleeve enclosing the first flexible body, the first sleeve having a first stiffness,
a second flexible body having a proximal region attached to the distal region of the first flexible body,
a second flexible sleeve enclosing the second flexible body, the second flexible sleeve being joined to the first flexible sleeve adjacent the distal region of the first flexible body, thereby forming a junction, the second flexible sleeve having a second stiffness different than the first stiffness creating a step discontinuity in stiffness between the first and second bodies,
a transition assembly in the distal region of the first flexible body and the proximal region of the second flexible body and underlying the junction between the first and second flexible sleeves to create a graduated transition in stiffness between the first and second flexible sleeves, and
a flexible material having a tensile strength greater than the first and second flexible sleeves underlying the junction.

11. A catheter according to claim 10
wherein the second flexible body carries at least one electrode.

12. A catheter according to claim 10
wherein the second flexible body carries at least one radio frequency transitting ablation electrode.

13. A catheter according to claim 10
and further including an element to flex the second flexible element relative to the first flexible element.

14. A catheter according to claim 6 or 10
wherein the second stiffness is less than the first stiffness.

15. A catheter comprising
a first flexible body having a first stiffness, the body having a distal region,
a second flexible body having a proximal region attached to the distal region of the first flexible body at a junction, the second flexible body having a second stiffness less than the first stiffness creating a step discontinuity in stiffness between the first and second bodies, and
a transition assembly in distal region of the first flexible body and the proximal region of the second flexible body to form a graduated transition in stiffness between the first and second bodies by increasing the stiffness of the second flexible body over a region extending distally from the junction, the transition assembly comprising a first tube over the distal region of the first flexible body and a second tube extending over the first tube and extending farther to overlap a portion of the proximal region of the second flexible body.

16. A catheter according to claim 15
wherein the second flexible body carries at least one electrode.

17. A catheter according to claim 15
wherein the second flexible body carries at least one radio frequency transitting ablation electrode.

18. A catheter according to claim 15
and further including an element to flex the second flexible element relative to the first flexible element.

19. A catheter comprising
a first flexible body having a distal region,
a first flexible sleeve enclosing the first flexible body, the first sleeve having a first stiffness,
a second flexible body having a proximal region attached to the distal region of the first flexible body,
a second flexible sleeve enclosing the second flexible body, the second flexible sleeve being joined to the first flexible sleeve adjacent the distal region of the first flexible body, thereby forming a junction, the second flexible sleeve having a second stiffness less than the first stiffness creating a step discontinuity in stiffness between the first and second sleeves, and
a transition assembly in the distal region of the first flexible body and the proximal region of the second flexible body and underlying the junction between the first and second flexible sleeves to create a graduated transition in stiffness between the first and second flexible sleeves by increasing the stiffness of the second flexible sleeve over a region extending distally from the junction, the transition assembly comprising a first tube underlying a portion of the first and second flexible sleeves at the junction and enclosing the distal region of the first flexible body, a second tube over the first tube and overlapping a portion of the proximal end of the second flexible body, both the first and second tubes underlying the junction.

20. A catheter according to claim 19
and further including a flexible material having a tensile strength greater than the first and second flexible sleeves attached to the second tube and underlying the junction.

21. A catheter according to claim 19
wherein the second flexible body carries at least one electrode.

22. A catheter according to claim 19
wherein the second flexible body carries at least one radio frequency transitting ablation electrode.

23. A catheter according to claim 19
and further including an element to flex the second flexible element relative to the first flexible element.

24. A method for manufacturing a catheter, comprising:
providing a first flexible body having a first stiffness, the first flexible body having a distal region,
providing a second flexible body having a proximal region, the second flexible body having a second stiffness less than the first stiffness,
joining the proximal region of the second flexible body to the distal region of the first flexible body, thereby creating a step discontinuity in stiffness between the first and second bodies, and
providing a graduated transition in stiffness between the first and second bodies by attaching a transition assembly having a first portion underlying the distal region of the first flexible body and a second portion underlying the proximal region of the second flexible body to thereby increase the stiffness of the second flexible body in the region where the first and second flexible bodies join.

25. A method for manufacturing a catheter comprising the steps of provinding a first flexible body having a distal region, providing a second flexible body having a proximal region, joining the distal region of the first flexible body to the proximal region of the second flexible body, enclosing the first flexible body with a first flexible sleeve having a first stiffness, enclosing the second flexible body in a second flexible sleeve having a second stiffness less than the first stiffness, joining the second flexible sleeve to the first flexible sleeve adjacent the distal region of the first flexible body, thereby forming a junction, and providing a graduated transition in stiffness between the first and second sleeves at the junction by attaching a transition assembly to the distal region of the first flexible body and the proximal region of the second flexible body, the transition assembly underlying the junction.

26. A method according to claim 25 and further including the step of attaching to the transition sleeve assembly beneath the junction a flexible material having a tensile strength greater than the first and second flexible sleeves.

* * * * *